United States Patent [19]

Achini et al.

[11] 4,164,583

[45] Aug. 14, 1979

[54] BENZ[F]ISOINDOLINE COMPOUNDS

[75] Inventors: Roland Achini, Therwil; Wolfgang Oppolzer, Vandoeuvres; Emil Pfenninger, Allschwil, all of Switzerland

[73] Assignee: Sandoz Ltd., Basle, Switzerland

[21] Appl. No.: 917,948

[22] Filed: Jun. 22, 1978

[30] Foreign Application Priority Data

Jun. 28, 1977 [CH] Switzerland .......................... 7916/77
Jun. 28, 1977 [CH] Switzerland .......................... 7917/77

[51] Int. Cl.$^2$ ...................... A61K 31/40; C07D 209/62
[52] U.S. Cl. .................................. 424/274; 260/326.1; 260/326.5 R; 260/326.62; 260/465 E; 260/465.5 R; 260/556 A; 260/556 AR; 260/558 R; 260/558 D; 260/559 R; 260/561 HL; 260/651 R; 560/24; 560/30; 560/32; 568/655
[58] Field of Search ...................... 260/326.1; 424/274

[56] References Cited

U.S. PATENT DOCUMENTS

| | | | |
|---|---|---|---|
| 2,740,795 | 4/1956 | Wenner | 260/326.1 |
| 3,890,347 | 6/1975 | Middlemiss | 260/326.1 |
| 3,973,030 | 8/1976 | Bowman et al. | 424/274 |
| 4,014,899 | 3/1977 | Bowman et al. | 260/325 PH |

FOREIGN PATENT DOCUMENTS 827087 9/1975 Belgium .

*Primary Examiner*—Alton D. Rollins
*Attorney, Agent, or Firm*—Gerald D. Sharkin; Robert S. Honor; Timothy G. Rothwell

[57] ABSTRACT

The present invention provides benz[f]isoindolines, useful in the treatment of aggression, a process for their preparation and compositions containing these compounds.

14 Claims, No Drawings

BENZ[F]ISOINDOLINE COMPOUNDS

The present invention relates to benz[f]isoindolines useful in the treatment of aggression, a process for their preparation and compositions containing these compounds.

More particularly, the present invention provides compounds of formula I,

[Structure I: naphthalene fused with isoindoline ring, R$_1$ on aromatic ring, R$_2$ on central position, N—R$_3$ on isoindoline nitrogen]

wherein
R$_1$ is hydrogen, fluorine, chlorine, bromine, alkyl of 1 to 4 carbon atoms or alkoxy of 1 to 4 carbon atoms,
R$_2$ is hydrogen or alkyl of 1 to 4 carbon atoms, and
R$_3$ is hydrogen or alkyl of 1 or 2 carbon atoms.

In one group of compounds R$_1$ is hydrogen. R$_1$ can also be fluorine, chlorine or bromine. Additionally, R$_1$ can be alkyl of 1 to 4 carbon atoms or alkoxy of 1 to 4 carbon atoms.

When R$_2$ is alkyl of 1 to 4 carbon atoms, this is preferably ethyl or methyl, especially methyl.

R$_2$ and R$_3$ are especially preferred to be independently hydrogen or methyl.

The invention further provides a process for the production of a compound of formula I comprising, (a) producing a compound of formula Ia,

[Structure Ia: similar to I with N—R$_3'$]

wherein
R$_1$ and R$_2$ are as previously defined and
R$_3'$ is alkyl of 1 or 2 carbon atoms, by dehydrating a compound of formula II,

[Structure II: tetrahydro form with HO and R$_2$ on central carbon, N—R$_3'$]

wherein
R$_1$, R$_2$ and R$_3'$ are as previously defined, or (b) producing a compound of formula Ib,

[Structure Ib: same as I with NH]

wherein
R$_1$ and R$_2$ are as previously defined, by removing a group Z, hereinafter defined, from a compound of formula III,

[Structure III: same as I with NZ]

wherein
R$_1$ and R$_2$ are as previously defined and
Z is a removable acyl group.

Process variant (a) can be effected according to known methods, for example in the presence of a mineral acid such as hydrochloric acid or in the presence of a strong organic acid such as trifluoroacetic acid, or with acetic anhydride, thionyl chloride or phosphorus oxychloride. The reaction may conveniently be effected at an elevated temperature, for example at the boiling temperature, of the reaction mixture.

Z is preferably R$_4$SO$_2$ or R$_5$CO, wherein
R$_4$ is alkyl of 1 to 4 carbon atoms, phenyl or p-tolyl and
R$_5$ is hydrogen, alkyl of 1 to 4 carbon atoms, CF$_3$, phenyl, C$_{1-4}$alkoxy, phenoxy or benzyloxy.

The removal of Z, in process variant (b), can be effected according to known methods.

The removal of an R$_5$CO group can conveniently be effected by acid or alkaline hydrolysis.

The alkaline hydrolysis can, for example, be effected using a 1 to 5 N solution of an alkali metal hydroxide such as sodium or potassium hydroxide. Suitable solvents include, for example, lower alcanols, especially methanol and ethanol. When R$_5$CO is an easily removable acyl group, for example trifluoroacetyl or benzyloxycarbonyl, the hydrolysis can be effected either at room temperature or at a slightly elevated temperature. The hydrolysis is completed within a period of from about ½ to about 2 hours. When R$_5$CO is a less easily removable acyl group, for example, ethoxycarbonyl, the reaction is best carried out at an elevated temperature, preferably under reflux. The reaction is completed within a period of from about 10 to about 20 hours.

The acid hydrolysis can, for example, be effected using 2 N hydrochloric acid, advantageously at an elevated temperature, especially at the reflux temperature of the reaction mixture.

When Z is R$_4$SO$_2$, this can be removed under reductive conditions, in manner analogous to known methods, for example with sodium dihydro bis-(2-methoxyethoxy) aluminate, or hydrolytically, for example with phenol in 40% hydrobromic acid/acetic acid.

The resulting compounds of formula I may be isolated and purified using conventional techniques.

Free base forms of the compounds of formula I may be converted into acid addition salt forms and vice versa in conventional manner. Suitable acids for producing acid addition salt forms include mineral acids such as hydrochloric acid and organic acids such as maleic and fumaric acids.

The starting materials of formula II can, for example, be obtained as follows:
(a) By alkylating an amine of formula IV, $$NC—CH_2—CH_2—NHR_3' \qquad IV$$

wherein
R$_3'$ is a previously defined, with a cinnamyl halide of formula V, $$\underset{R_1}{\underset{|}{\text{C}_6\text{H}_4}}-\text{CH}=\text{CH}-\text{CH}_2-\text{Hal} \qquad \text{V}$$

wherein
R₁ is as previously defined,
in the presence of a base, such as NaOH, or in an excess of the amine of formula IV. The alkylation in the presence of NaOH may coveniently be effected in a water/methylene chloride mixture with the addition of a phase transfer catalyst such as benzyl-tri-(n-butyl) ammonium bromide.

(b) The resulting compound of formula VI,

[Structure VI: R₁-phenyl-CH=CH-CH₂-N(R₃')-CH₂-CN]

is cyclised using a base, for example NaH in hexamethyl phosphoric acid triamide or NaOC₂H₅ in dimethyl formamide to produce a compound of formula VII,

[Structure VII: bicyclic intermediate with R₁, NC, N-R₃']

(c) Hydrolysis and cyclisation of the compound of formula VII in the presence of an acid such as polyphosphoric acid, yields a compound of formula VIII,

[Structure VIII: tricyclic ketone with R₁, N-R₃', C=O]

(d) (i) When R₂ is hydrogen: reduction of the ketone of formula VIII to the alcohol of formula IXa,

[Structure IXa: tricyclic alcohol with R₁, N-R₃', OH]

for example with complex metal hydrides, such as LiAlH₄ or NaBH₄, in a suitable solvent such as ether, tetrahydrofuran or ethanol;

(d) (ii) When R₂ is alkyl: reaction with an organometallic compound, e.g. R₂'MgHal or R₂'Li, wherein R₂' is alkyl of 1 to 4 carbon atoms, and subsequent hydrolysis to provide an alcohol of formula IXb,

[Structure IXb: tricyclic alcohol with R₁, N-R₃, HO, R₂']

The compounds of formula IV and V are either known or may be prepared by known methods.

The starting materials of formula III can, for example, be obtained by thermal cyclisation of a compound of formula Xa,

[Structure Xa: R₁-phenyl-CH=CH-CH(Cl)(R₂)-...-N-Z]

or Xb

[Structure Xb: R₁-phenyl-CH=CH-CH₂-N-Z with R₂ branch]

The thermal cyclisation can be effected in an inert organic solvent, preferably having a high boiling point, such as dichlorobenzene. The reaction is preferably effected under acid free conditions at a temperature of from 160°–190° C.

The compounds of formula Xa and Xb can, for example, be obtained by reacting a compound of formula XI,

[Structure XI: R₁-phenyl-CH=CH-CH₂-NHZ]

with a compound of formula XIIa, $$\underset{\text{Cl}}{\underset{|}{\text{R}_2-\text{C}}}=\text{CH}-\text{CH}_2-\text{Hal} \qquad \text{XIIa}$$

or with a compound of formula XIIb, $$\text{R}_2-\text{C}\equiv\text{C}-\text{CH}_2\text{Hal} \qquad \text{XIIb}$$

for example, in the presence of NaH in hexamethylphosphoric acid triamide.

The compounds of formulae XI, XIIa and XIIb are either known or may be produced according to known methods.

In the following Examples, all temperatures are in degrees Celsius.

EXAMPLE 1:
6-Chloro-9,9a-dihydro-2,4-dimethylbenz[f]-isoindoline

A solution of 14 g of 6-chloro-3a,4,9,9a-tetrahydro-2,4-dimethylbenz[f]isoindolin-4-ol in 140 ml of trifluoroacetic acid is stirred for one hour at room temperature and then evaporated. The residue is taken up in ice cold aqueous sodium hydroxide solution, extracted with methylene chloride, the organic phase dried over sodium sulphate and the solution evaporated. The title compound is obtained by crystallisation from methanolic hydrochloric acid/ether. M.P. 253°–255° (Hydrochloride salt form).

The following compounds can be obtained in manner analogous to that of Example 1, using appropriate starting materials in approximately equivalent amounts.

EXAMPLE 2:
9,9a-Dihydro-2-methylbenz[f]isoindoline

M.P. 219°–229° (Decomp. Hydrochloride salt form).

EXAMPLE 3:
9,9a-Dihydro-2,4-dimethylbenz[f]isoindoline

M.P. 205°–206°. (Hydrogen fumarate salt form)

EXAMPLE 4:
6-Chloro-9,9a-dihydro-2-methylbenz[f]isoindoline

M.P. 211°–212°. (Hydrogen fumarate salt form).

EXAMPLE 5:
2-Ethyl-9,9a-dihydro-4-methylbenz[f]isoindoline

M.P. 237°–239° (Decomp. Hydrochloride salt form)

EXAMPLE 6:
9,9a-dihydro-8-methoxy-2-methylbenz[f]isoindoline

M.P. 185°–187° (Decomp. Hydrogen fumarate salt form).

The starting material employed in Example 1 can be prepared as follows:

(a) A solution of 116 g of p-chlorocinnamyl bromide in 500 ml of methylene chloride is added dropwise with stirring to a mixture of 42 g of 3-methylamino-propionitrile and 8.9 g of benzyl-tri-(n-butyl)ammonium bromide in 1 liter of methylene chloride and 500 ml of 2 N sodium hydroxide solution at room temperature and under a nitrogen atmosphere, and the emulsion stirred for 65 hours at room temperature. The organic phase is separated, washed with water, dried over sodium sulphate and evaporated to yield 3-[N-(p-chlorocinnamyl)-methylamino]-propionitrile. M.P. 143° [hydrogen oxalate form]

(b) 252 g of 3-[N-(p-chlorocinnamyl)-methylamino]-propionitrile in 1 liter of hexamethylphosphoric acid triamide (HMPT) are added dropwise over a period of 1¼ hours at 0°–5° and in a nitrogen atmosphere to a suspension of 36 g of sodium hydride (80% in mineral oil) in 2 liter of HMPT, and the mixture stirred at room temperature for a period of 16 hours. Water is then added to the mixture with ice cooling, the mixture extracted with ether, the organic phase washed with water, dried over sodium sulphate and evaporated to yield 4-(p-chlorobenzyl)-1-methylpyrrolidin-3-carbonitrile. M.P. 170°–172° [hydrogen oxalate form].

(c) 25 ml of water are added dropwise to 500 g of polyphosphoric acid at 50° followed by 50 g of 4-(p-chlorobenzyl)-1-methyl-pyrrolidin-3-carbonitrile and the mixture stirred for 1 hour at 125° and then for 2½ hours at 160°. Ice and 1 liter of 50% sodium hydroxide are added to the cooled mixture which is then extracted with ethyl acetate. The organic phase is washed with water, dried over sodium sulphate and evaporated to yield 6-chloro-3a,4,9,9a-tetrahydro-2-methylbenz[f]isoindolin-4-one. M.P. 148°–150° (hydrogen maleate form).

(d) A solution of 43 g of 6-chloro-3a,4,9,9a-tetrahydro-2-methylbenz[f]isoindolin-4-one in 430 ml of tetrahydrofuran is added dropwise at room temperature with stirring to 170 ml of a ca. 5% solution of methyl lithium in ether in a nitrogen atmosphere and the mixture is stirred for 5½ hours at room temperature. Thereafter, saturated ammonium chloride solution and water are added and the mixture extracted with methylene chloride. The organic phase is dried over sodium sulphate and evaporated. The residue is crystallised from ether/petroleum ether to yield 6-chloro-3a,4,9,9a-tetrahydro-2,4-dimethylbenz[f]-isoindolin-4-ol. M.P. 125°–130°.

The starting material required for the preparation of the title compound of Example 4 can be produced as follows:

(e) 1.6 g of sodium borohydride in 20 ml of ethanol are added at 0°–5° to a solution of 10 g of 6-chloro-3a,4,9,9a-tetrahydro-2-methylbenz[f]isoindolin-4-one in 100 ml of ethanol, stirred at room temperature for a further hour, water is added and the mixture evaporated. The residue is taken up in 10% tartaric acid, the aqueous phase extracted with ether, mixed with 2 N caustic soda solution and extracted with ethyl acetate. The ethyl acetate phase is dried over sodium sulphate and evaporated. The residue is crystallised from methylene chloride/pentane to yield 6-chloro-3a,4,9,9a-tetrahydro-2-methylbenz[f]isoindolin-4-ol. M.P. 178°–182°.

EXAMPLE 7: 9,9a-Dihydrobenz[f]isoindoline

A mixture of 10 g of 9,9a-dihydrobenz[f]isoindolin-2-trifluoroacetamide and 50 ml of 3 N potassium hydroxide in methanol is left to stand at room temperature for 16 hours, the solution evaporated, the residue taken up in water and extracted with ether. The ethereal phase is dried over sodium sulphate and evaporated. The residue is evaporated with methanolic hydrogen chloride and crystallised from methanol/ether to yield the title compound. M.P. 240°–248°. (Hydrochloride salt form).

The 9,9a-dihydrobenz[f]isoindolin-2-trifluoroacetamide used as starting material, can be prepared as follows:

(a) A solution of 250 g of N-cinnamyltrifluoroacetamide in 1 liter of hexamethylphosphoric acid triamide (HMPT) is added dropwise with ice-cooling and stirring under a nitrogen atmosphere, to a suspension of 27 g of sodium hydride in 400 ml of HMPT. After the evolution of gas has ceased, a solution of 130 g of 1,3-dichloropropene and 1 g of sodium iodide in 1 liter of HMPT is added dropwise and the mixture stirred for 16 hours at room temperature. The reaction mixture is then poured on to water and extracted with ether. The ethereal solution is dried over sodium sulphate, evaporated and the oily residue chromatographed on 3.5 kg of silica gel with toluene to yield N-(3-chloro-2-propenyl)-N-cinnamyl-trifluoroacetamide as an oil.

(b) A solution of 267 g of N-(3-chloro-2-propenyl)-N-cinnamyl-trifluoroacetamide in 5.5 liter of o-dichlorobenzene are refluxed in an argon atmosphere for 30 hours and finally evaporated. The residue is chromatographed on 6 kg of silica gel with toluene. Recrystallisation from methylene chloride/ether yields 9,9a-dihydrobenz[f]-isoindolin-2-trifluoroacetamide. M.P. 150°–155°.

The following compounds can be obtained in manner analogous to that described in Example 7 employing appropriate starting materials in approximately equivalent amounts.

EXAMPLE 8:
9,9a-Dihydro-4-methylbenz[f]isoindoline

M.P. 224°–226° (hydrogen fumarate form)

EXAMPLE 9:
9,9a-Dihydro-6-methylbenz[f]isoindoline

M.P. 116°–118°.

The compounds of formula I are useful because they possess pharmacological activity in animals. In particular, the compounds possess anti-aggressive activity, and are therefore useful for the treatment of aggression, for example in the sedation of psychopaths and mentally retarded patients, as indicated in standard tests, for example in that according to the method of H.C.Y. Yen et al. [J. Pharmacol. Exp. Ther. 122, 85 A, (1958)] involving the aggression of mice induced by isolation, on p.o. administration of from about 0.1 to about 10 mg/kg of animal body weight.

For this use, the dosage will, of course, vary depending on the compound employed, mode of administration and treatment desired. However, in general, satisfactory results are obtained when administered at a daily dosage of from about 0.015 to about 10 mg/kg of animal body weight, conveniently given in divided doses 2 to 4 times a day or in sustained release form. For the larger mammals, the total daily dosage is in the range of from about 1 to about 30 mg, and dosage forms suitable for oral administration comprise from about 0.25 to about 15 mg of the compounds admixed with a solid or liquid pharmaceutical carrier.

Additionally, at higher doses, the compounds of formula I are useful as sedatives by virtue of their effect on the central nervous system, as indicated in standard tests, for example in the climbing test in mice on p.o. administration of from about 5 to about 150 mg/kg of animal body weight. Owing to their effect on the central nervous system, the compounds may be used in the psychiatric treatment of agitation.

For this use, the dosage will, of course, vary depending on the compound involved, mode of administration and treatment desired. However, in general, satisfactory results are obtained when administered at a daily dosage of from about 0.15 to about 100 mg/kg of animal body weight, conveniently given in divided doses, 2 to 4 times a day or in sustained release form. For the larger mammals, the total daily dosage is in the range of from about 10 to about 200 mg, and dosage forms suitable for oral administration comprise from 2.5 to about 100 mg of the compounds admixed with a solid or liquid pharmaceutical diluent or carrier.

The compounds of formula I may be administered in pharmaceutically acceptable acid addition salt forms. Such forms exhibit the same order of activity as the free base forms and are readily prepared in conventional manner. Representative acids for acid addition salt formation include hydrochloric and fumaric acids. The present invention also provides a pharmaceutical composition comprising a compound of formula I, in free base form or in the form of a pharmaceutically acceptable acid addition salt, in association with a pharmaceutically acceptable diluent or carrier. Such compositions may be in the form of, for example, a solution or a capsule.

What we claim is
1. A compound of formula I,

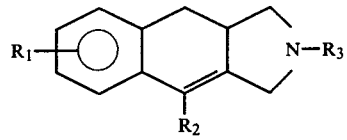

wherein
$R_1$ is hydrogen, fluorine, chlorine, bromine, alkyl of 1 to 4 carbon atoms or alkoxy of 1 to 4 carbon atoms,
$R_2$ is hydrogen or alkyl of 1 to 4 carbon atoms, and
$R_3$ is hydrogen or alkyl of 1 or 2 carbon atoms,
in free base form or in pharmaceutically acceptable acid addition salt form.

2. 9,9a-Dihydro-2,4-dimethylbenz[f]isoindoline.

3. A pharmaceutical composition comprising a compound of claim 1, in association with a pharmaceutically acceptable diluent or carrier.

4. A method of treating aggression in animals which comprises administering a therapeutically effective amount of a compound of claim 1 to an animal in need of such treatment.

5. A method of sedating an animal which comprises administering a therapeutically effective amount of a compound of claim 1 to an animal in need of such treatment.

6. A compound of the formula

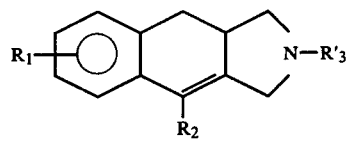

wherein
$R'_3$ is alkyl of 1 or 2 carbon atoms; and
$R_1$ and $R_2$ are as defined in claim 1.

7. A compound of the formula

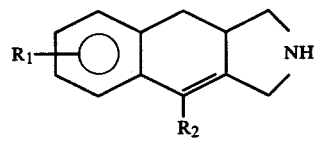

wherein
$R_1$ and $R_2$ are as defined in claim 1.

8. The compound of claim 1 which is 9,9a-dihydro-2-methylbenz[f]isoindoline.

9. The compound of claim 1 which is 6-chloro-9,9a-dihydro-2-methylbenz[f]isoindoline.

10. The compound of claim 1 which is 2-ethyl-9,9a-dihydro-4-methylbenz[f]isoindoline.

11. The compound of claim 1 which is 9,9a-dihydro-8-methoxy-2-methylbenz[f]isoindoline.

12. The compound of claim 1 which is 9,9a-dihydrobenz[f]isoindoline.

13. The compound of claim 1 which is 9,9a-dihydro-4-methylbenz[f]isoindoline.

14. The compound of claim 1 which is 9,9a-dihydro-6-methylbenz[f]isoindoline.

* * * * *